(12) United States Patent
Vilhelmsen et al.

(10) Patent No.: US 11,291,352 B2
(45) Date of Patent: Apr. 5, 2022

(54) METHOD FOR MANUFACTURING A TIP HOUSING

(71) Applicant: Ambu A/S, Ballerup (DK)

(72) Inventors: Erik Øllgaard Vilhelmsen, Espergærde (DK); Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 579 days.

(21) Appl. No.: 16/352,437

(22) Filed: Mar. 13, 2019

(65) Prior Publication Data

US 2019/0282070 A1 Sep. 19, 2019

(30) Foreign Application Priority Data

| Mar. 14, 2018 | (EP) | ................................. | 18161746 |
| Mar. 14, 2018 | (EP) | ................................. | 18161752 |
| Mar. 14, 2018 | (EP) | ................................. | 18161762 |
| Mar. 11, 2019 | (EP) | ................................. | 19161893 |
| Mar. 11, 2019 | (EP) | ................................. | 19161898 |
| Mar. 11, 2019 | (EP) | ................................. | 19161907 |

(51) Int. Cl.

| *A61B 1/00* | (2006.01) |
| *B29C 45/16* | (2006.01) |
| *A61B 1/06* | (2006.01) |
| *A61B 1/07* | (2006.01) |

(Continued)

(52) U.S. Cl.
CPC ........ *A61B 1/00137* (2013.01); *A61B 1/0008* (2013.01); *A61B 1/0011* (2013.01); *A61B 1/00096* (2013.01); *A61B 1/00103* (2013.01); *A61B 1/0684* (2013.01); *A61B 1/07* (2013.01); *B29C 45/16* (2013.01); *B29K 2995/0026* (2013.01); *B29L 2031/753* (2013.01); *G02B 23/2476* (2013.01)

(58) Field of Classification Search
None
See application file for complete search history.

(56) References Cited

U.S. PATENT DOCUMENTS

| 4,496,211 A | 1/1985 | Daniel |
| 4,533,243 A | 8/1985 | Zhukov et al. |
| 4,805,596 A | 2/1989 | Hatori |

(Continued)

FOREIGN PATENT DOCUMENTS

| DE | 19815598 | 10/1999 |
| DE | 10010931 | 9/2001 |

(Continued)

OTHER PUBLICATIONS

Extended Search Report dated Apr. 2, 2019 in related EP Application No. 19161893.3.

(Continued)

*Primary Examiner* — Timothy J Neal
(74) *Attorney, Agent, or Firm* — Faegre Drinker Biddle & Reath LLP (57) ABSTRACT

A method for manufacturing a tip housing for the distal tip of a vision device such as an endoscope is disclosed. The method includes providing a molding tool, introducing in the molding tool a first housing material, introducing in the molding at least one further housing material different from the first housing material, allowing the at least one further housing material to set and form a combined housing component with the first molding material, and removing the combined housing component from the molding tool.

17 Claims, 7 Drawing Sheets

(51) Int. Cl.
  *B29L 31/00* (2006.01)
  *G02B 23/24* (2006.01)

(56) References Cited

U.S. PATENT DOCUMENTS

| | | | |
|---|---|---|---|
| 4,923,276 | A | 5/1990 | Wells |
| 5,193,525 | A | 3/1993 | Silverstein et al. |
| 5,193,526 | A | 3/1993 | Daikuzono |
| 5,325,845 | A | 7/1994 | Adair |
| 5,408,572 | A | 4/1995 | Kriege |
| 5,718,663 | A | 2/1998 | Wulfsberg |
| 5,873,877 | A | 2/1999 | McGaffigan et al. |
| 5,928,136 | A | 7/1999 | Barry |
| 5,993,378 | A | 11/1999 | Lemelson |
| 7,662,094 | B2 | 2/2010 | Iddan |
| 8,414,480 | B2 | 4/2013 | Kendale et al. |
| 8,485,966 | B2 | 7/2013 | Robertson |
| 8,790,250 | B2 | 7/2014 | Petersen et al. |
| 8,948,560 | B1 | 2/2015 | Wach |
| 9,220,400 | B2 | 12/2015 | Petersen |
| 9,521,942 | B2 | 12/2016 | Robertson |
| 9,622,649 | B2 | 4/2017 | Lin |
| 9,633,649 | B2 | 4/2017 | Lin |
| 9,854,962 | B2 | 1/2018 | McGrail et al. |
| 10,245,402 | B2 | 4/2019 | Daher et al. |
| 10,321,804 | B2 | 6/2019 | Jacobsen et al. |
| 10,835,103 | B2 | 11/2020 | Tamura et al. |
| 2003/0227547 | A1 | 12/2003 | Iddan |
| 2004/0064018 | A1 | 4/2004 | Dunki-Jacobs et al. |
| 2004/0199052 | A1 | 10/2004 | Banik et al. |
| 2004/0242963 | A1 | 12/2004 | Matsumoto et al. |
| 2005/0046807 | A1 | 3/2005 | Hanano |
| 2005/0049462 | A1 | 3/2005 | Kanazawa |
| 2005/0203341 | A1 | 9/2005 | Welker et al. |
| 2007/0249907 | A1 | 10/2007 | Boulais et al. |
| 2008/0242935 | A1 | 10/2008 | Inoue |
| 2009/0054728 | A1 | 2/2009 | Trusty |
| 2009/0177040 | A1 | 7/2009 | Lyons et al. |
| 2009/0209819 | A1 | 8/2009 | Kitagawa et al. |
| 2009/0292168 | A1 | 11/2009 | Farr |
| 2010/0217082 | A1 | 8/2010 | Ito |
| 2010/0286475 | A1 | 11/2010 | Robertson |
| 2011/0118549 | A1 | 5/2011 | Han |
| 2012/0041268 | A1 | 2/2012 | Grey et al. |
| 2012/0323078 | A1 | 12/2012 | Kikumori et al. |
| 2013/0175720 | A1 | 7/2013 | Otsuka et al. |
| 2013/0271588 | A1 | 10/2013 | Kirma et al. |
| 2013/0329433 | A1 | 12/2013 | Lin et al. |
| 2014/0081085 | A1 | 3/2014 | Takato et al. |
| 2014/0328047 | A1 | 11/2014 | Kamee et al. |
| 2015/0036146 | A1 | 2/2015 | Staloff |
| 2015/0335227 | A1 | 11/2015 | Jacobsen et al. |
| 2016/0106306 | A1 | 4/2016 | Furuta |
| 2017/0245734 | A1 | 8/2017 | Kaneko |
| 2018/0084981 | A1 | 3/2018 | Wang |
| 2018/0140172 | A1 | 5/2018 | Hu et al. |
| 2018/0310890 | A1 | 11/2018 | Li |
| 2019/0033506 | A1 | 1/2019 | Weber et al. |
| 2019/0175007 | A1 | 6/2019 | Sørensen et al. |
| 2019/0227298 | A1 | 7/2019 | Elmaanaoui |
| 2019/0282077 | A1 | 9/2019 | Srensen et al. |
| 2019/0313891 | A1 | 10/2019 | Oka |
| 2019/0350442 | A1 | 11/2019 | Giessen et al. |
| 2019/0374092 | A1 | 12/2019 | Wu et al. |
| 2020/0110256 | A1 | 4/2020 | Altshuler et al. |
| 2021/0127955 | A1 | 5/2021 | Sorensen et al. |

FOREIGN PATENT DOCUMENTS

| | | |
|---|---|---|
| DE | 102018110620 | 7/2019 |
| JP | 3764512 B2 | 4/2006 |
| JP | 2009-125528 A | 6/2009 |
| JP | 2018-015250 A | 2/2018 |
| JP | 2018015250 A | 2/2018 |
| WO | WO 2005/023099 A1 | 3/2005 |
| WO | WO2009/100368 | 8/2009 |
| WO | 2010/066790 A1 | 6/2010 |
| WO | WO2010/066790 | 6/2010 |
| WO | 2014/106511 A1 | 7/2014 |
| WO | WO2017/104048 | 6/2017 |
| WO | WO2018/059643 | 4/2018 |

OTHER PUBLICATIONS

Extended Search Report dated Apr. 2, 2019 in related EP Application No. 19161907.1.
Extended Search Report dated Apr. 2, 2019 in related EP Application No. 19161898.2.
Extended search report dated Oct. 15, 2018 in related EP Application No. 18161752.3.
Extended search report dated Oct. 15, 2018 in related EP Application No. 18161762.2.
Extended search report dated Oct. 26, 2018 in related EP Application No. 18161746.5.
OEE—Intention to Grant under Rule 71(3), dated Dec. 23, 2020 in related EP Application No. 19161907.1, including specification, claims, and drawings.
Search report from European Application No. 19 161 898.2 dated Jul. 1, 2021; 5 pgs.
Extended European search report issued in European application No. 19161893.3, dated Jul. 5, 2019.

METHOD FOR MANUFACTURING A TIP HOUSING

CROSS-REFERENCE TO RELATED APPLICATIONS

This patent application claims priority to and the benefit of European Patent Applications Nos. 18161752 and 18161762, entitled A TIP PART FOR A VISION DEVICE, filed on Mar. 14, 2018, of European Patent Application No. 18161746, entitled METHOD FOR MANUFACTURING A TIP HOUSING, filed on Mar. 14, 2018, of European Patent Application No. 19161898, entitled A TIP PART FOR A VISION DEVICE, filed on Mar. 11, 2019, of European Patent Application No. 19161907, entitled A TIP PART FOR AN INSERTABLE VISION DEVICE, filed on Mar. 11, 2019, and of European Patent Application No. 19161893, entitled METHOD FOR MANUFACTURING A POT-SHAPED TIP HOUSING, filed on Mar. 11, 2019, respectively, all of which are incorporated by reference herein in their entirety.

TECHNICAL FIELD

The present disclosure relates to a component to be used in insertable medical vision devices, in particular disposable insertion endoscopes, and more specifically to a housing for the tip of the disposable insertion endoscope and the manufacture thereof.

BACKGROUND

Vision devices, such endotracheal tubes and insertion endoscopes are well known devices for visually inspecting body cavities, such as body cavities. Typically, an insertion endoscope comprises an elongated insertion tube with a handle at the proximal end as seen from the operator and visual inspections means, such as a built-in camera, at the distal end of the elongated insertion tube. Electrical wiring for the camera and other electronics such as Light Emitting Diode (LED) lighting, accommodated in the tip part at the distal end run along the inside of the elongated insertion tube from the handle to the tip part. Instead of using cameras, endoscopes may also be fiber-optic, in which case the optical fibers run along inside of the elongated insertion tube to the tip part.

In order to be able to maneuver the endoscope inside the body cavity, the distal end of the endoscope may comprise a bending section with increased flexibility, e.g. a number of articulated segments of which the tip part forms the distal-most segment. This is typically done by tensioning or slacking pull wires also running along the inside of the elongated insertion tube from the tip part through the remainder of articulated segments to a control mechanism of the handle. Furthermore, a working channel may run along the inside of the insertion tube from the handle to the tip part, allowing liquid to be removed from the body cavity or allowing the insertion of surgical instruments or the like into the body cavity.

As the name indicates, endoscopes, are used for seeing inside things, such as lungs or other body cavities of a patient. Modern endoscopes are therefore typically equipped with a least one camera or similar image capturing device at the distal tip of the endoscope. Provided that sufficient light is present, this allows the operator to see where the endoscope is steered and to set the target of interest once the tip has been advanced thereto. This therefore normally requires illumination of the area in front of the distal tip of the endoscope, in particular the field of vision of the camera(s). One known way of achieving such illumination is to provide the above mentioned LED lighting using one or more Light Emitting Diodes (LEDs) in the tip of the endoscope, as e.g. mentioned in WO2014/106511, disclosing a disposable endoscope.

When the insertion tube of the endoscope is intended to be inserted into a body cavity, the insertion tube needs to be sealed in a watertight manner. This is in particular the case for the distal tip part because it accommodates the camera, LED(s) and other delicate electronics, prone to malfunction or destruction if exposed to humidity.

One known way of sealing the tip part of an endoscope is disclosed in WO2010/066790. In this document a transparent monolithic housing is formed around the electronics and working channel by placing the electronics and the tube forming the working channel in a mold of transparent material, such as silicone. A transparent UV curable resin is then inserted from the bottom of the mold to avoid bubbles to form in the transparent resin. Because the resin rises slowly from the bottom, the air is slowly expelled from top of the mold, without any risk of air bubbles being trapped in the mold. The resin is then cured using UV irradiation through the transparent mold to form the monolithic housing. However, forming a monolithic housing in this way has some drawbacks. One is that it is a somewhat slow process. Another is that it can be difficult to position and maintain the components precisely in position during the insertion of the resin. Thus, the camera or LEDs may in few cases be off-set sideways or a thin transparent layer may inadvertently be created in front of the camera and/or LEDs, thereby reducing the imaging qualities of the tip part. This will lead to the product being discarded in the quality control, thereby increasing overall cost of manufacturing.

A further problem is the general transparency of the housing, which derives from that fact that the resin itself is and—needs to be, transparent in order for the UV radiation to penetrate and cure the resin. This may result in undesired stray light from the LEDs which through the transparent housing itself impinges on the sensor of the camera and may disturb the captured images.

This reflection problem is addressed in JP3-764512B. This document discloses a disposable external sleeve for the insertion tube of an insertion endoscope. The external sleeve has a tip part with a front window for the camera of the insertion endoscope. The front window of the tip part is provided with shading members through two component injection molding of a transparent window material and an opaque shading material. This is to minimize glare from the built-in light sources of sleeve to the camera of the insertion endoscope. This front window is generally just a pane with a uniform thickness apart from the shading members, and will not be well suited for an integral housing directly accommodating the components of the endoscope.

Furthermore, the materials which have good optical properties in terms of refraction index and transparency may not have good adhesion properties for e.g. sealant material, glue used for attaching outer sheaths or similar that involves adhesion.

It is a first object of the disclosure to provide a housing for a tip part of an endoscope, a tip part including such housing, and an endoscope with such a housing for the tip part which do not suffer from the above drawbacks.

SUMMARY

According to a first aspect of the invention this object is achieved by a tip housing for the distal tip of a disposable insertion endoscope, said tip housing having a front end and a circumferential wall and comprising a first polymer material and a second polymer material where the second polymer material is transparent, said tip housing being adapted to accommodate an electronic vision device, and at least one light source, said tip housing comprising a first window part arranged in front of the electronic vision device in the field of view thereof and a second window part arranged in front of the at least one light source, wherein the first window part and the second window parts are formed as a single piece of said second polymer material, said tip housing further comprising an inwardly protruding part, where the inwardly protruding part is formed integrally with the circumferential wall as a single piece of the first polymer material and/or integrally with said first and second window parts as a single piece of the second polymer material.

According to a first embodiment according to the first aspect of the disclosure the inwardly protruding part is adapted to guide and position the electronic vision device with respect to said first window part. This is an efficient way of assuring good positioning and alignment of the electronic vision device with respect to the first window part, so as to ensure low rejection rates in the manufacture of the disposable insertion endoscopes, in turn keeping costs down.

According to a second embodiment of the first aspect of the disclosure, the at least one inwardly protruding part formed integrally with said first and second window parts as a single piece of the second polymer material comprises a light guide. By integration of the light guides in the single-piece item also comprising the first and second windows, the angular light distribution from LED light sources may readily be adapted to the field of view of the electronic vision device.

According to another embodiment according to the first aspect of the disclosure, the first housing material is opaque. This allows the introduction of shading parts inter alia reducing stray light and glare into the camera.

According to a further embodiment according to the first aspect of the disclosure, the set first material has better adhesion properties to glue than the set second material. This allow the circumferential wall of housing to adhere efficiently to a sealing glue for sealing the inner compartment, and for an outer sheath of the insertion tube of the endoscope to be securely adhered to the exterior or the interior of the circumferential wall of the pot-shape housing.

According to yet another embodiment according to the first aspect of the disclosure, at the front end of the housing, said single piece of said first polymer material partially covers said second polymer, so that the front window part and said light guide part appear as separate areas isolated from each other by said first polymer, when viewed from the distal end. This has been found to highly reduce stray light and glare from the light source(s) into the camera.

According to yet a further embodiment according to the first aspect of the disclosure, the second housing material is a thermoplastic material. This allows the tip housing to be produced in an efficient manner, such as by injection molding.

According to a second aspect of the disclosure the object is solved by a method for manufacturing a tip housing according to the first aspect of the disclosure for the distal tip of an insertion endoscope, said method comprising providing a molding tool, introducing in the molding tool a first housing material, introducing in the molding at least one second housing material different from the first housing material, allowing the at least one second housing material to set and form a combined housing component with the first molding material, removing the combined housing component from the molding tool.

This allows the provision of an integrated unit for the tip housing having different areas with different desired properties.

According to a first embodiment, the molding tool comprises a first cavity, a second cavity and a core. In particular, in injection molding this is advantageous as the molded object normally shrinks during cooling and therefore tends to stick to the core.

According to another embodiment, the first housing material is allowed to set before the at least one second housing material is introduced. This provides well defined boundaries between the two materials in the final integrated unit. Moreover, it allows the first mold to stick to the core for the introduction into the second cavity of the molding tool.

According to another embodiment, the volume of the at least one second housing material introduced in the mold is smaller than the volume of the first housing material introduced in the mold. This is in particular of advantage when the second material is more brittle than the first material, because having a smaller volume thereof will make it less prone to stick to the mold due to shrinking, thereby making it easier to extract from the mold. Therefore, the second material may also be injected at higher pressure than the first material, because a high pressure used for the first material would make it more prone to sticking to the mold and/or cores, in turn making removal more difficult.

According to a further embodiment, the at least one second housing material is selected from the group comprising thermoplastic materials, thermoset materials and elastomers. These materials render themselves for injection molding of at least the second housing material. Injection molding is efficient in terms of quick reproduction of identical items.

Accordingly, according to another embodiment, the introduction of the first and/or the second housing material forms part of an injection molding process.

According to another embodiment, the at least one second housing material comprises a transparent housing material. Injecting the transparent material as the second housing material in many cases is advantageous, because the transparent materials which are preferred for their optical properties, may then be introduced under higher pressure than the first material. This, in turn, reduces shrinking and better control of the optical properties of the final product is therefore obtained. Furthermore, because the more brittle material constitutes only a minority part of the total housing material, it is easier to remove from the mold. Accordingly, it is also preferred when the first housing material is opaque.

Albeit the first housing material could also be selected for other properties, such as good adhesion to sealant materials and adhesives. Thus, according to a further embodiment, the set first material has better adhesion properties to glue than the second material.

According to another embodiment, first cavity and the second cavity have generally cylindrical shapes. This results in a generally cylindrical tip housing which in turn is suitable for the endoscopes made with tip housing according to the present disclosure.

BRIEF DESCRIPTION OF THE DRAWINGS

The disclosure will now be described in greater detail based on nonlimiting exemplary embodiments and with reference to the drawings on which.

DETAILED DESCRIPTION

Figure 19:
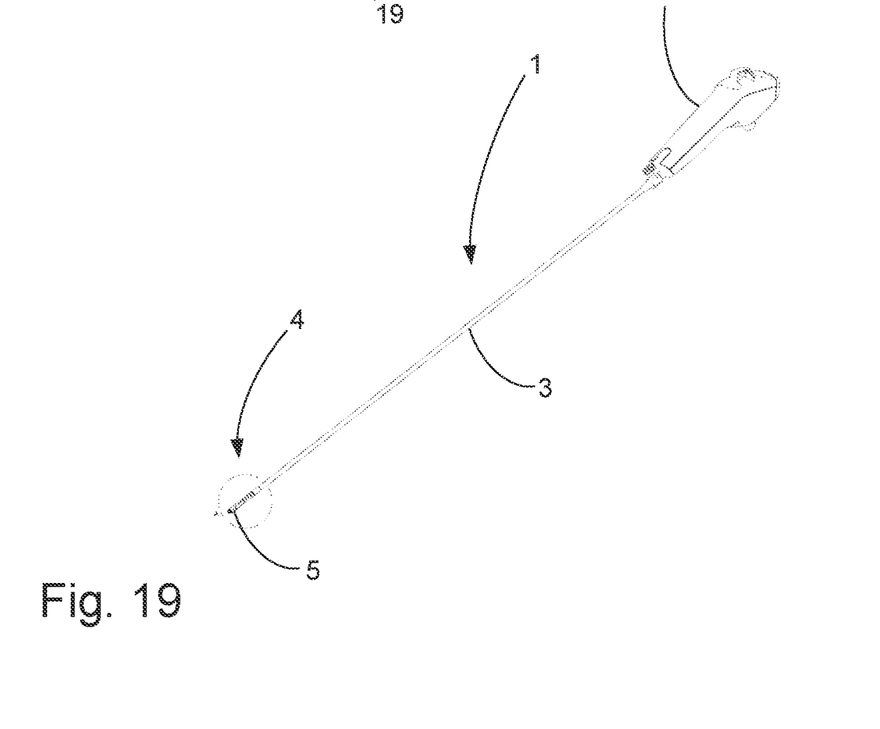
FIG. 19 shows an endoscope with a distal tip part in accordance with one embodiment of the disclosure.

Turning first to FIG. 19, an endoscope 1 comprises a handle 2 at the proximal end, an insertion tube 3 extending towards the distal end where it comprises an articulated bending section 4, which as the most distal segment has a distal tip part 5. Though omitted for illustration purposes the articulated bending section 4 will normally be covered by a suitable sleeve, connected at least at its own distal end to the distal tip part 5, e.g. by means of an adhesive. This as such is conventional and e.g. known from the aforementioned WO2014/106511. The endoscope 1 is intended as a disposable endoscope. That is to say, it is to be thrown away after use with a single patient, rather than cleaned and re-used, and low manufacturing costs is therefore an important issue.

Figure 2:
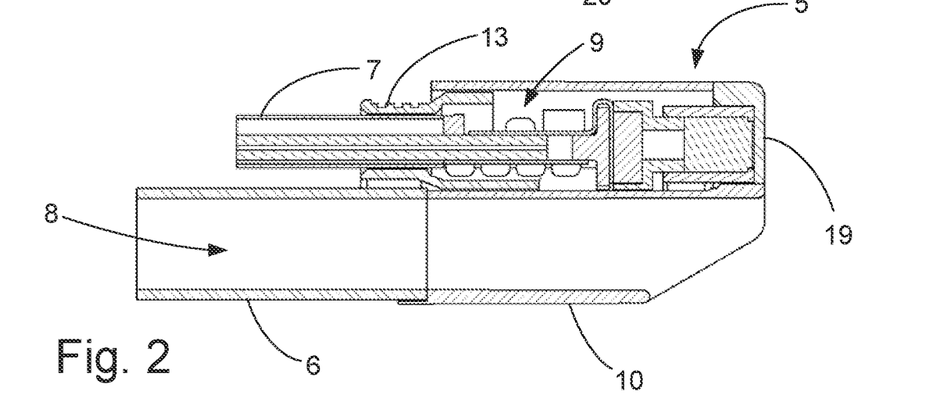
FIG. 2 shows a cross-section of the distal tip part of FIG. 1 taken along the line II-II.

In FIG. 2 the distal tip part 5 can be seen in greater detail. Two tubular members 6, 7 leads to the tip part from the proximal handle 2. The first tubular member 6 provides a working channel 8 for the endoscope 1. The second tubular member 7 serves as a conduit for electrical cables and/or optical fibers and/or illumination fibers, depending on which kind of illumination and imaging the endoscope 1 relies on. In the illustrated embodiment, the imaging and illumination relies on an electronics section 9 with LEDs and a video camera accommodated in a compartment the distal tip part 5, but the disclosure is not limited thereto. Rather, the present disclosure relates to the tip housing 10 rather than the details of what is accommodated therein.

Figure 3:
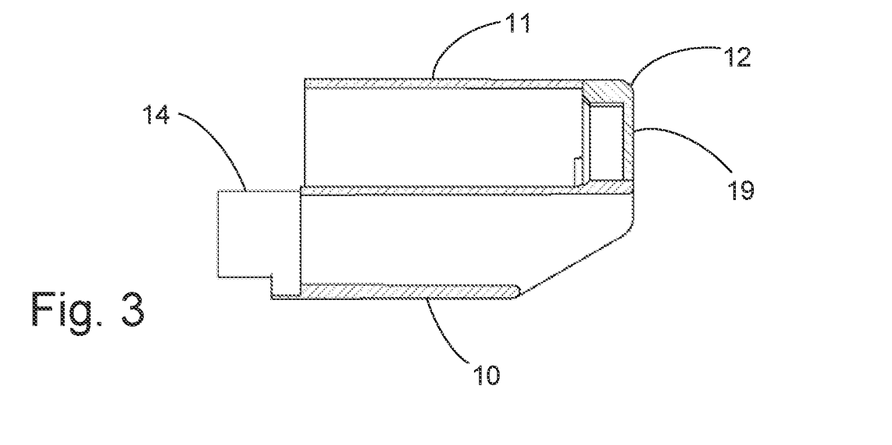
FIG. 3 shows a cross-section corresponding to that of FIG. 3 of the housing part of the distal tip only.

In FIG. 3 the tip housing 10 is shown on its own. The housing 10 is generally pot-shaped, although a passage may be provided through it to serve as an extension of a tube 6 forming part of a working channel 8. As will be noticed from the different hatchings as well as the exploded views of FIGS. 4 and 5, the tip housing comprises two different materials 11, 12. To keep cost down, both of these materials are preferably polymer materials, in particular thermoplastic materials suitable for injection molding, but also thermoset materials and/or elastomers can be used. The second material 12 is a transparent material allowing light from the light source(s) such as LED(s) to pass and illuminate objects beyond the distal end of the endoscope 1. Accordingly, the second material 12 should have good optical properties, e.g. in terms of transparency and high index of refraction. However, not all materials render themselves for economically feasible manufacture and the use in environments for which the endoscope is intended. The second material 12 is therefore preferably an injection moldable polymer material such as polycarbonate, but other thermoplastic materials such as COP, COC and PMMA are also envisaged as are thermoset materials such as LSR (Liquid Silicone Rubber). One advantage of such softer and/or more elastic materials is their impact resistance. A softer and/or more elastic material would also allow for an increase in the transverse dimensions of the core 16 as the softer and/or more elastic material would yield during withdrawal thereof from the mold cavity 17 in the molding process described below.

The first material 11 on the other hand need not have good optical properties and may therefore be selected based on entirely different criteria.

In particular the first material may be an opaque material. This will allow stray light from e.g. the light source to be absorbed and not disturb the images captured by the vision receptor, be it a video camera, an imaging chip, or an optical fiber. If opacity is the only desire, the first material 11 may essentially be the same as the second material 12, i.e. the same plastic material with a filler or a dye to make it opaque. This ensures that the first and second materials are very compatible, allowing them to bond well together and ensure a water and air tight housing part 5.

Also, the first material 11 may also be chosen for good adhesion properties to other materials, e.g. other parts of the endoscope 1. Such good adhesion properties could be good bonding to sealant materials, used for sealing the proximal end of the housing, e.g. around the lead-in 13 for electrical cables to the electronics section 9, to prevent ingress of water and other pollutants that could potentially harm the electronics section 9. Also, good bonding to an adhesive used for attaching the external sleeve around the bending section is advantageous.

Furthermore, the first material may be soft at least compared to the second material. In particular, it may be so soft that rather than attaching a sleeve to it, it may itself form a sleeve for the articulated bending section 4 to which it is attached as the most distal segment. Furthermore, this would facilitate or enable demolding of undercut features inside the housing because the material may deform elastically.

Evidently, there are numerous other design choices that come into play for the selection of the most suitable material for the first material 11, provided of course that no further materials are used. The latter is, however, far from excluded by the present disclosure. Thus, if for the attachment of the tubular member 6 a number of spring like protrusions 14 are provided for holding the end of the tubular member 6, the material should be resilient enough to provide sufficient holding force, but of course with suitable adhesive properties, the tubular member could also be glued to the inside of the protrusions 14 or a similar receptacle.

To achieve good tightness between the first material 11 and the second material 12 they are according to the disclosure molded together to form one integrated unit. A molding process for this will be described below with reference to FIGS. 6 to 13.

Figures 6, 7, 8:
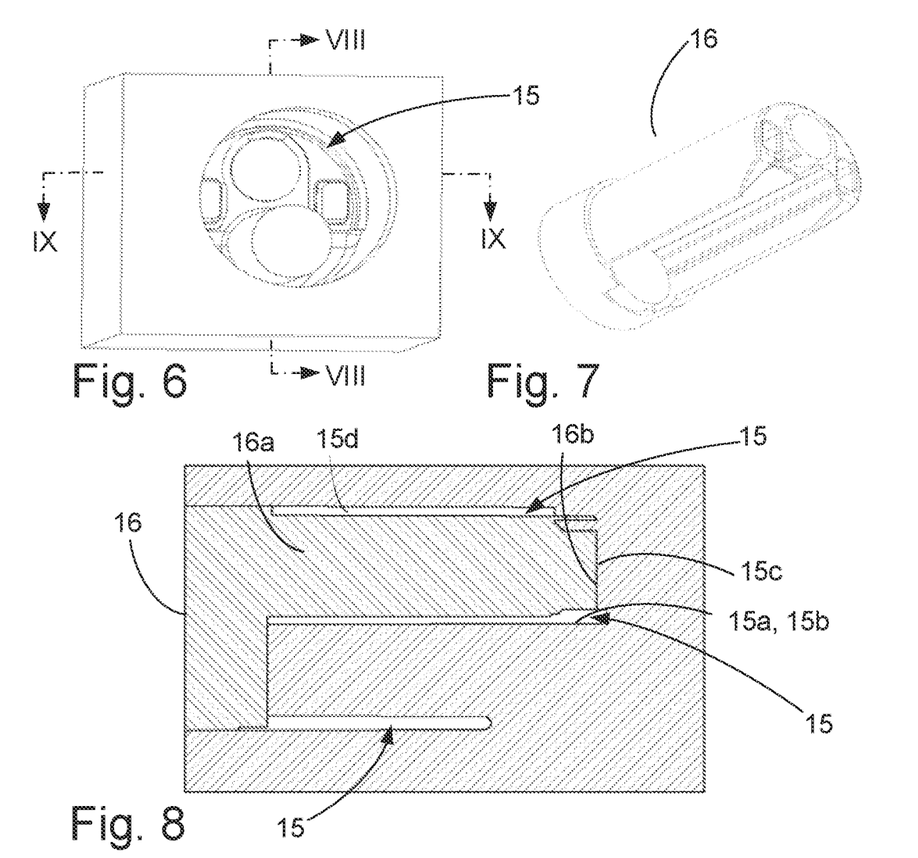
FIG. 6 shows an isometric view of a first mold cavity for the use in manufacturing the housing part of FIGS. 1 to 5.
FIG. 7 shows an isometric view of a core for the use in manufacturing the housing part of FIGS. 1 to 5.
FIG. 8 shows a cross-section along the line VIII-VIII of FIG. 6 with the core inserted.
Figure 9:
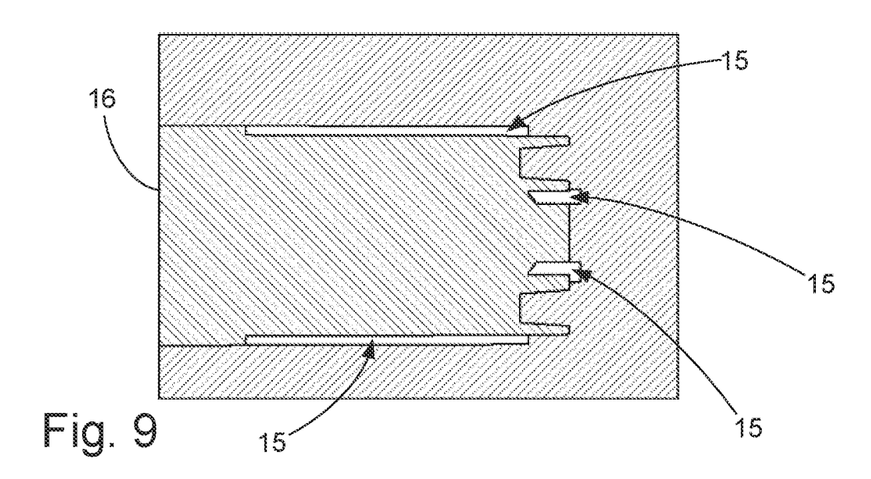
FIG. 9 shows a cross-section along the line IX-IX of FIG. 7 with the core inserted.
Figure 10:
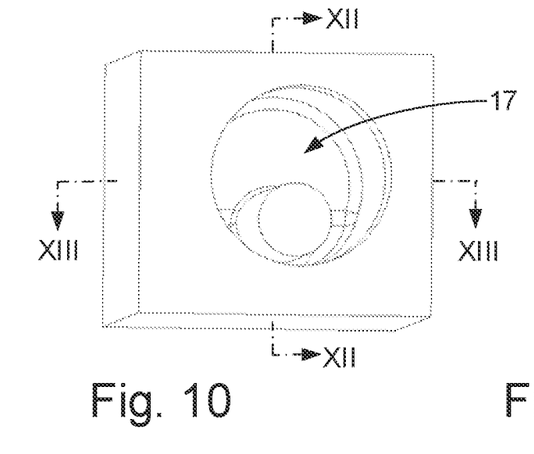
FIG. 10 shows an isometric view of a second mold cavity for the use in manufacturing the housing part of FIGS. 1 to 5.
Figure 11:
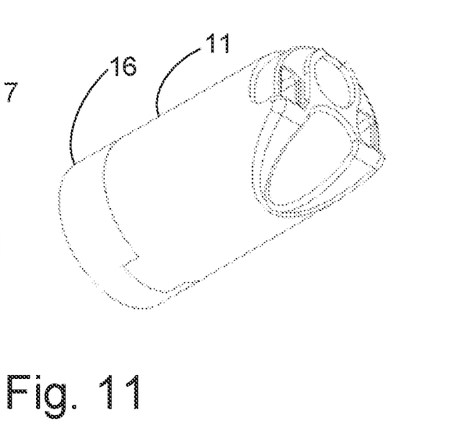
FIG. 11 shows the core of FIG. 7 with a first housing part attached.

Turning first to FIG. 6, an isometric view of a generally cylindrical first mold cavity 15 forming part of molding tool for the use in the molding process is shown, albeit only schematically as inlets and the like have been omitted. The first mold cavity 15 includes a first cavity surface (the surface of the mold defining the first mold cavity) which includes a circumferential wall surface 15b and a window surface 15c. The molding tool further comprises a core 16 adapted to be inserted into the first mold cavity to form a first configuration of the molding tool as illustrated in the cross-sections of FIGS. 8 and 9, defining a first spacing 15d therebetween. The core 16 includes an elongate portion 16a and core window surface 16b. Assuming that the first material is a thermoplastic material, then in this first configuration the hot liquefied first material 11 is injected into the mold cavity 15 under a suitable pressure. When the liquefied first material 11 cools and solidifies it shrinks as most material do when they cool. Thus, when, after the cooling, the core 16 is removed from the first mold cavity 15 the solidified first material 11 will stick to the core 16 and be removed with it. This is in particular the case if additional first material 11 is not injected under sustained pressure during the cooling stage. FIG. 11 shows the core 16 with the first material 11 stuck to it. If the first material is a thermoset material it will instead be injected in a cold state and subsequently heated to set or vulcanize the material.

Figure 12:
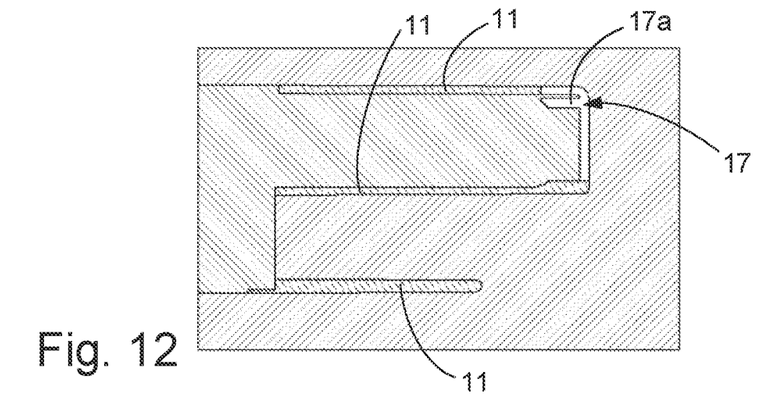
FIG. 12 shows a cross-section along the line XII-XII of FIG. 10 with the core inserted.
Figure 13:
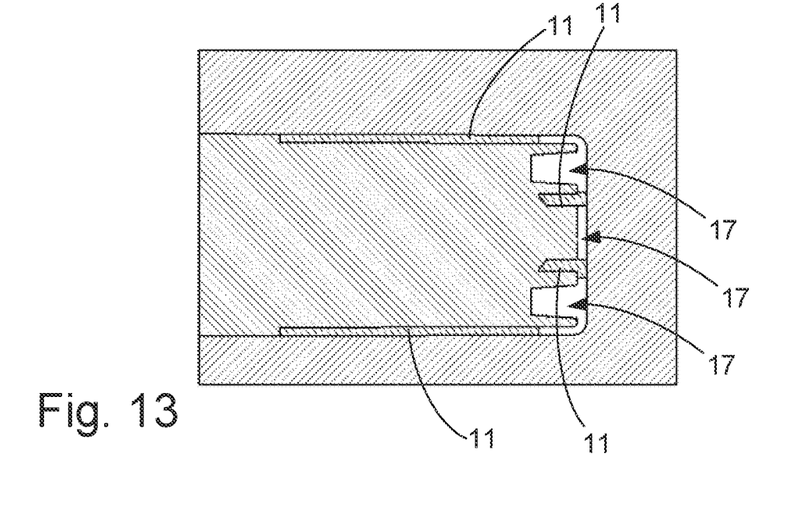
FIG. 13 shows a cross section along the line XIII-XIII of FIG. 10 with the core inserted.

The core 16 with the first material stuck to it is then used as a what is effectively a new core in a second generally cylindrical mold cavity 17 forming as second configuration of the molding tool, as can be seen in the cross-sections of FIGS. 12 and 13, defining a second spacing 17a therebetween. Here it will also be noted that in the embodiment the volume of the resulting cavity 17 is smaller than the volume of the cavity 15. Accordingly, the volume of the second material introduced in the second molding stage is smaller than the volume of the first material introduced in the first stage. Using a smaller volume results in a smaller part, in turn keeping the surface area with which it may adhere to the mold down. Filling the resulting cavity 15 at a higher pressure, and injecting additional second material as the second material cools, is therefore possible without the resulting housing sticking unnecessarily in the mold. The larger volume of the first material may be introduced at lower pressure ensuring that the shrinking material sticks to the core 16 rather than the mold, allowing for easy removal and reinsertion.

This remaining cavity can now be filled with the hot liquefied second material 12 which fuses with the first material 11 when it solidifies and forms an integral unit as the housing part 5. As described above in conjunction with the first material this may be a hot liquefied injection with subsequent cooling if the second material is a thermoplastic material or a cold injection with subsequent heating if the second material is a thermosetting material. Since this part formed from the second material 12 is located in front of the light source(s) and the vision receptor, be it a video camera, an imaging chip, or an optical fiber it is important to also ensure good optical properties of the finished part. Thus, the second material 12 is preferably injected under high pressure to ensure good filling of the cavity 17 without internal bubbles, and with sustained high pressure under the solidifying stage to avoid shrinking, which could deteriorate smoothness of the front surface and cause internal cavities. Furthermore, apart from the optical advantages gained form injecting the transparent second material 12 last, injecting this second material which will normally have a smaller volume is advantageous. This allows the above mentioned injection at higher pressures because the smaller volume decreases the risk of the shrinking material sticking to the core and/or molds, even if additional material is injected to compensate for the shrinking.

After the second material 12 has finished solidifying, the housing part 5 comprising the bonded together first and second materials 11, 12 still sticks to the core 16 and may be removed from the second molding cavity 17 with it, when the molding tool is opened by retracting the core 16. The finished housing part 5 may then be separated from the core 16 in a conventional manner by means of ejectors in the core 16 or in any other suitable manner, e.g. using a robot.

The molding tool may preferably comprise two identical cores for one set of first and second cavities. With a suitable alternation arrangement, e.g. a revolver, one core 16 may be used in the first molding cavity while simultaneously the other core 16 with the solidified first material 11 thereon is used in the second molding cavity and subsequently vice versa in an alternating manner. This arrangement may of course be multiplied with more sets of first and second cavities in sequence and a corresponding number of cores used in these cavities in one after the other.

Figure 5:
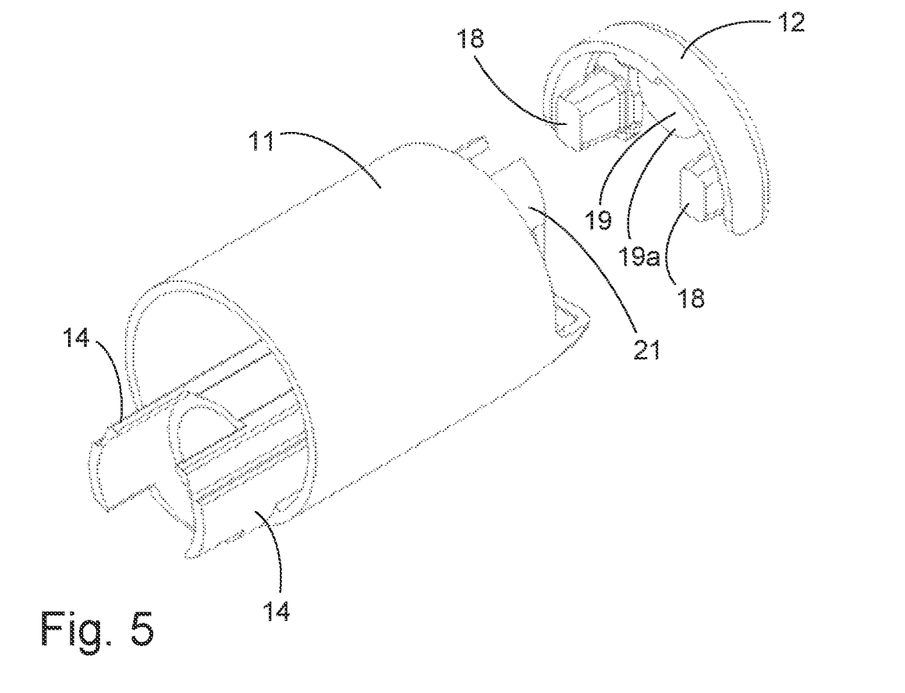
FIG. 5 shows a second exploded view of the housing part of FIG. 1.

The layout of the first and second molding cavities 15, 17 and the core 16 may differ from the illustrated embodiment resulting in a different housing part 10 for the tip part 5. Thus, either or both of first material and second material 12 could extend longer in the lengthwise direction i.e. from distal end towards proximal end. The layout of an opaque material could be shaped specifically to the output of the light sources. Likewise, the layout of the transparent material could be shaped specifically to the light sources. As best seen in FIG. 5 this could involve the transparent second material 12 comprising integrated light guides 18 behind emission surfaces 20, allowing the angular light distribution from LED light sources to be adapted to the field of view a video camera used as the image receptor. As can be seen the light guides in the present example are truncated pyramids with a generally rectangular cross-section which has been found useful for the rectangular image capture chip of a video camera. Also, the protective window 19 in front of the image receptor could comprise curved surfaces in order to act as a lens. As seen in FIG. 5, the window 19 has an inner surface 19a and the light guides 18 extend inwardly from a plane on which the inner surface 19a lies.

Figure 1:
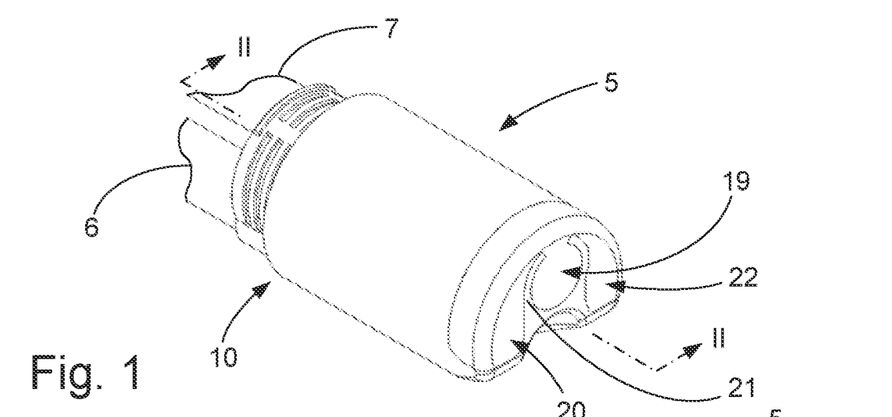
FIG. 1 shows an isometric view of a distal tip part of an endoscope with a housing part according to one embodiment of the present disclosure.
Figure 4:
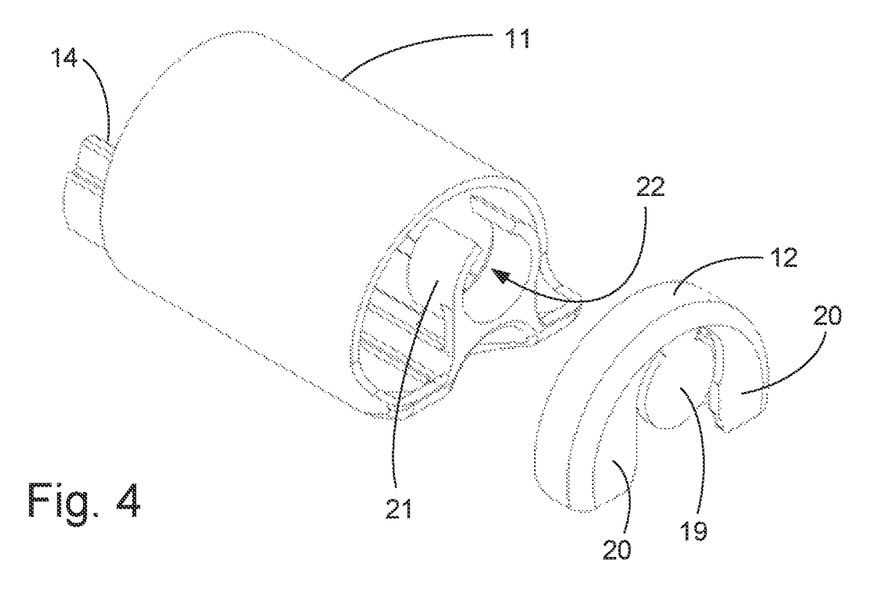
FIG. 4 shows a first exploded view of the housing part of FIG. 1.

As can be seen from FIG. 4 in conjunction with FIG. 1 the protective front window 19 is almost entirely surrounded by a C-shaped wall 21 protruding further inwardly from the distal end into the inner compartment of the tip housing 10. This C-shaped wall may fulfil plural functions. The primary function is to serve as a guide and alignment means, i.e. forming a receptacle 22 for the electronic vision device. An optional secondary function is to serve as a shading means preventing stray light from e.g. the emission surfaces 20 or the front surface of the second window parts 20, in general, to enter into the electronic vision device. In that case, the material from which the C-shaped wall 21 is made is coloured and/or opaque, preferably in a dark colour.

More specifically the layout of the first and second molding cavities 15, 17 and the core 16 could be laid out to provide a housing part 10 as illustrated in FIGS. 14 to 18. For easy identification features in FIGS. 14 to 18 corresponding to features already described in conjunction with the embodiment of housing 10 of FIGS. 1 to 5 will have the same reference numerals.

Figure 14:
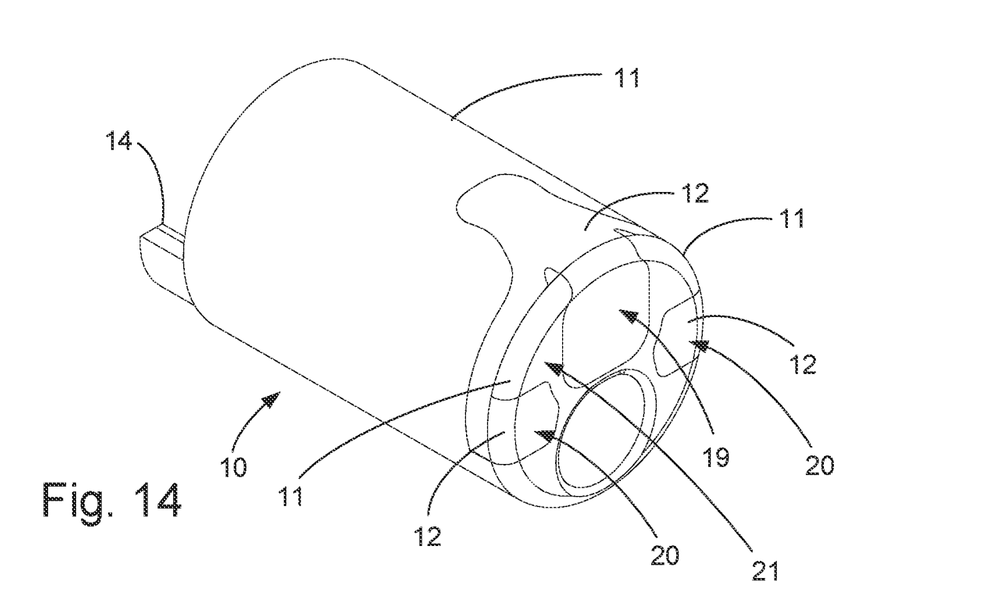
FIG. 14 shows an isometric view of a second embodiment of a housing part according to one embodiment of the present disclosure.
Figure 15:
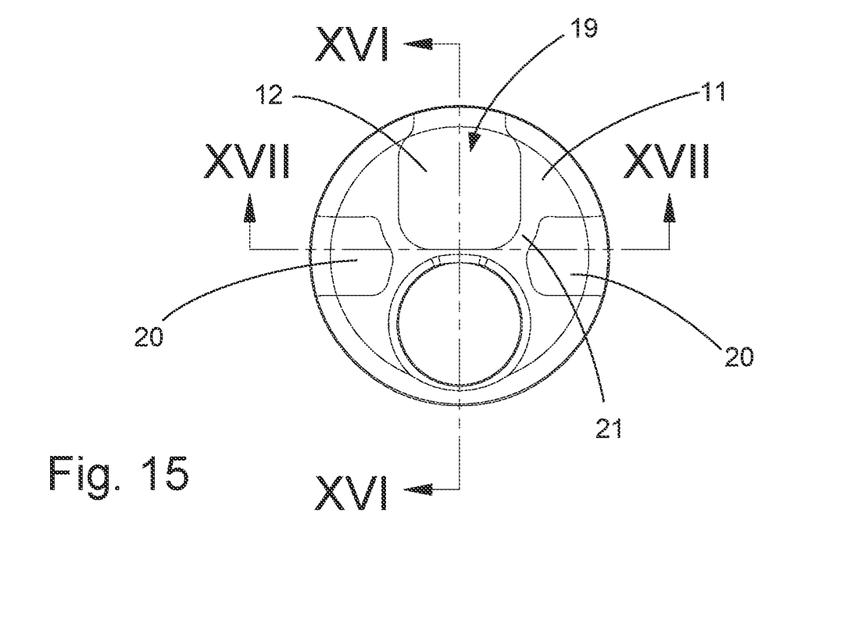
FIG. 15 shows a front view of the housing of FIG. 14.
Figure 16:
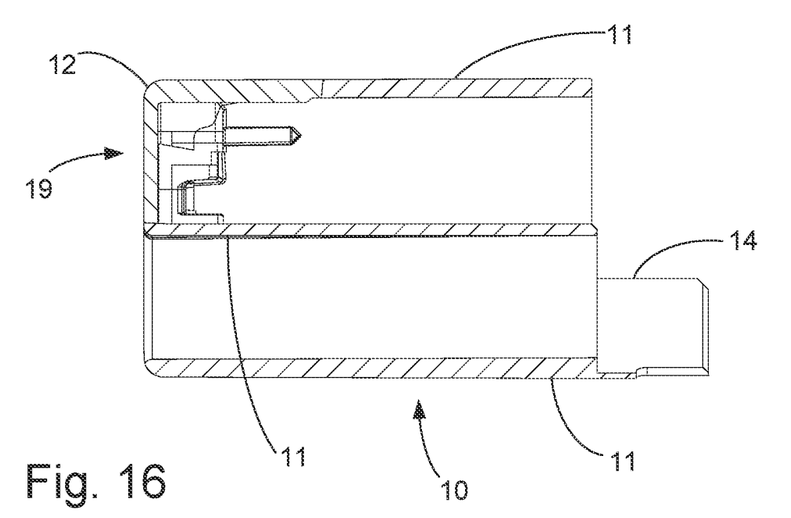
FIG. 16 shows a cross-sectional view of the housing of FIG. 14 along the line XVI-XVI of FIG. 15.
Figure 17:
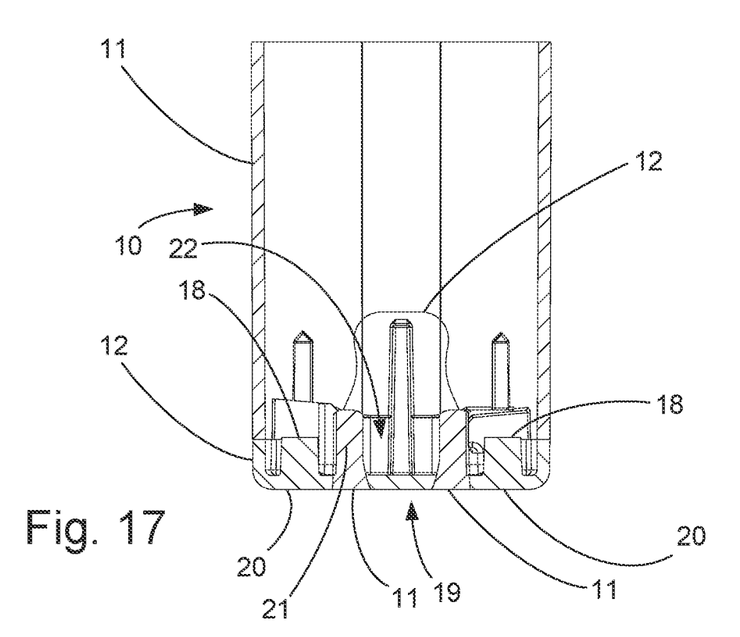
FIG. 17 shows a cross-sectional view of the housing of FIG. 14 along the line XVII-XVII of FIG. 15.
Figure 18:
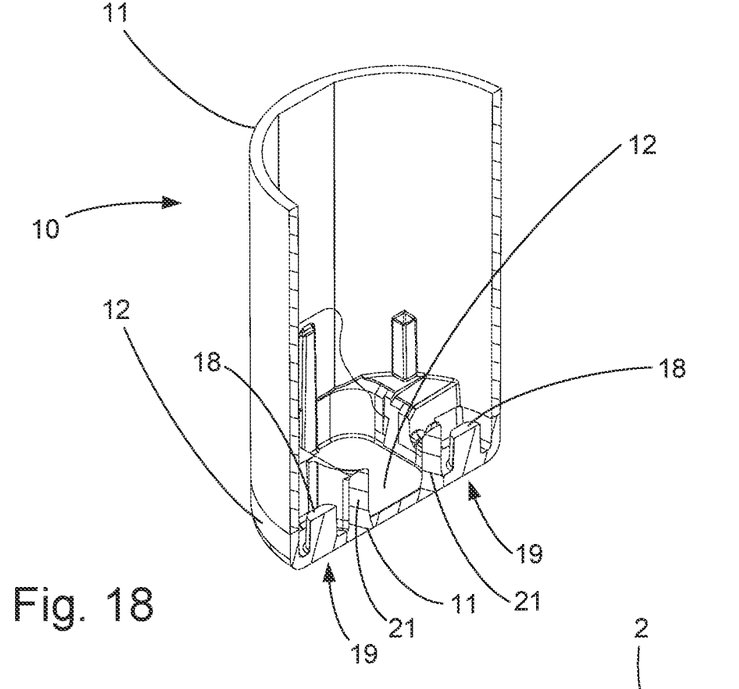
FIG. 18 shows an isometric view of a cross-sectional view of the housing of FIG. 14 taken also along the line XVII-XVII of FIG. 15.

Accordingly, in FIG. 14 a housing part 10 is shown. The housing part 10, as in the previously described embodiments, is generally pot-shaped to provide an inner compartment that may accommodate an electronics section 9 with LEDs and a video camera, etc. As an alternative to the LEDs the distal end of an optical fiber providing light from a remote light source could be accommodated in the compartment instead. The housing 10 is provided from two different materials preferably a first transparent material 11 and a second material 12 with different material properties, in this embodiment specifically opacity. This opacity may be used to reduce stray light from the light guides 18 in the emission surfaces 20 to the protective front window 19 in front of the camera and hence, the risk of glare disturbing the image captured by the camera.

More specifically, this has in the embodiment of FIGS. 14 to 18 been achieved by recessing parts of the second transparent material 12 with respect to the front surface and filling the recesses with the first opaque material 11. Thus, as seen from the front, said single piece of said first polymer material 11 from which the circumferential wall is made covers said second polymer material 12, so that the front window part 19 and the light guide parts 18, or at least the emission areas 20 in front of the light guide parts appear as separate areas isolated from each other by a shading part 21 made from said first polymer, when viewed from the distal end. That is to say the transparent areas appear as three isolated islands, isolated by the opaque material whereas in the first embodiments they appear as three peninsulas only partially isolated by the opaque material. In either of the two embodiments, a shading part 21 made in one single piece with the circumferential wall is thus provided.

Furthermore, even though the description above has been given for sequential molding it is not excluded that the housing part may be molded in a co-injection process where the first and second housing materials are introduced e.g. simultaneously into a single molding cavity through different inlets. This will allow control to be maintained over the location of the different materials without having to open, modify and reclose the mold, i.e. moving the cores 16 with respect to the molding cavities 15, 17.

With the housing part provided as an integral unit comprising two different materials it becomes possible to optimize the housing part for more than one parameter, e.g. for transparency vs. opacity, transparency vs. adhesion, brittleness vs. toughness, etc. The integral unit may be provided by other methods than the one described above. In particular, if injection molding is used, an opposite arrangement could be used, i.e. a single molding cavity, and two different cores inserted sequentially in that single molding cavity, the first molded part then remaining in the cavity when the second core is inserted. Analogous to the above, a number of identical cavities could then be used.

What is claimed is:

1. A method for manufacturing a tip housing for the distal tip of an endoscope, said method comprising:
   providing a molding tool comprising a first mold cavity and a core, the first mold cavity sized and shaped to receive the core, the first mold cavity having a first cavity surface including a circumferential wall surface and window surface, the core having an elongate portion with a core window surface at one end thereof, the core window surface shaped to abut the window surface of the first mold cavity when the core is inserted in the first mold cavity;
   inserting the core into the first mold cavity until the core window surface abuts the window surface, the core and the first mold cavity defining a first spacing therebetween configured to form a circumferential wall of the tip housing and a support wall defining a longitudinal receptacle;
   after inserting the core, introducing into the first spacing a first polymer material, the first polymer material being opaque;
   allowing the first polymer material to set and stick to the core;
   removing the core, with the first polymer material stuck to the core, from the first mold cavity;
   inserting the core, with the first polymer material stuck to the core, into a second mold cavity, the second mold cavity and the core defining a second spacing therebetween, the second spacing configured to form a window having an inner surface;
   introducing in the second spacing a second polymer material, the second polymer material being transparent; and
   allowing the second polymer material to fuse with the first polymer material and set to form the tip housing, the second polymer material forming the window at least in part within the longitudinal receptacle.

2. The method of claim 1, wherein the molding tool comprises the first mold cavity, the second mold cavity and the core.

3. The method of claim 1, wherein a volume of the second polymer material introduced in the second spacing is smaller than a volume of the first polymer material introduced in the first spacing.

4. The method of claim 1, wherein the second polymer material is selected from the group comprising thermoplastic materials, thermoset materials, and elastomers.

5. The method of claim 1, wherein the first mold cavity and the second mold cavity have generally cylindrical shapes.

6. The method of claim 1, wherein the introduction of the first and/or the second polymer material forms part of an injection molding process.

7. The method of claim 1, wherein introducing the second polymer material comprises introducing a first portion of the second polymer material and, as the first portion cools, introducing a second portion of the polymer material, wherein a total amount of the second polymer material is less than a total amount of the first polymer material.

8. The method of claim 7, wherein introducing the second polymer material is performed at a pressure sufficient to limit sticking of the second polymer material to the molding tool.

9. The method of claim 8, wherein introducing the second polymer material is performed with the pressure sufficient to limit sticking of the second polymer material maintained during cooling of the second polymer material.

10. The method of claim 1, wherein the first spacing is configured to form a first arcuate protrusion at an end of the first spacing opposite the end forming the window.

11. The method of claim 10, wherein the first spacing is configured to form the first arcuate protrusion and a second arcuate protrusion, the first arcuate protrusion and the second arcuate protrusion adapted to receive and retain a tube forming a working channel of the endoscope.

12. The method of claim 1, wherein introducing the first polymer material is performed with the first polymer material in hot liquid form.

13. The method of claim 1, wherein introducing the first polymer material is performed with the first polymer material in cold form, further comprising heating the first polymer material to cause it to stick to the core.

14. The method of claim 1, wherein the support wall extends inwardly further than the inner surface of the window, and wherein the support wall is adapted to receive in at least a part of the longitudinal receptacle a distal end of an electronic vision device.

15. The method of claim 1, wherein the second spacing is configured to form a light guide extending inwardly from a plane on which the inner surface of the window lies.

16. A tip housing for a distal tip of a disposable endoscope, said tip housing made according to the method of claim 1.

17. A disposable endoscope comprising a tip housing made according to the method of claim 1.

* * * * *